July 22, 1947. G. DE RUITER Plant Pat. 746
ROSE PLANT
Filed Dec. 8, 1942
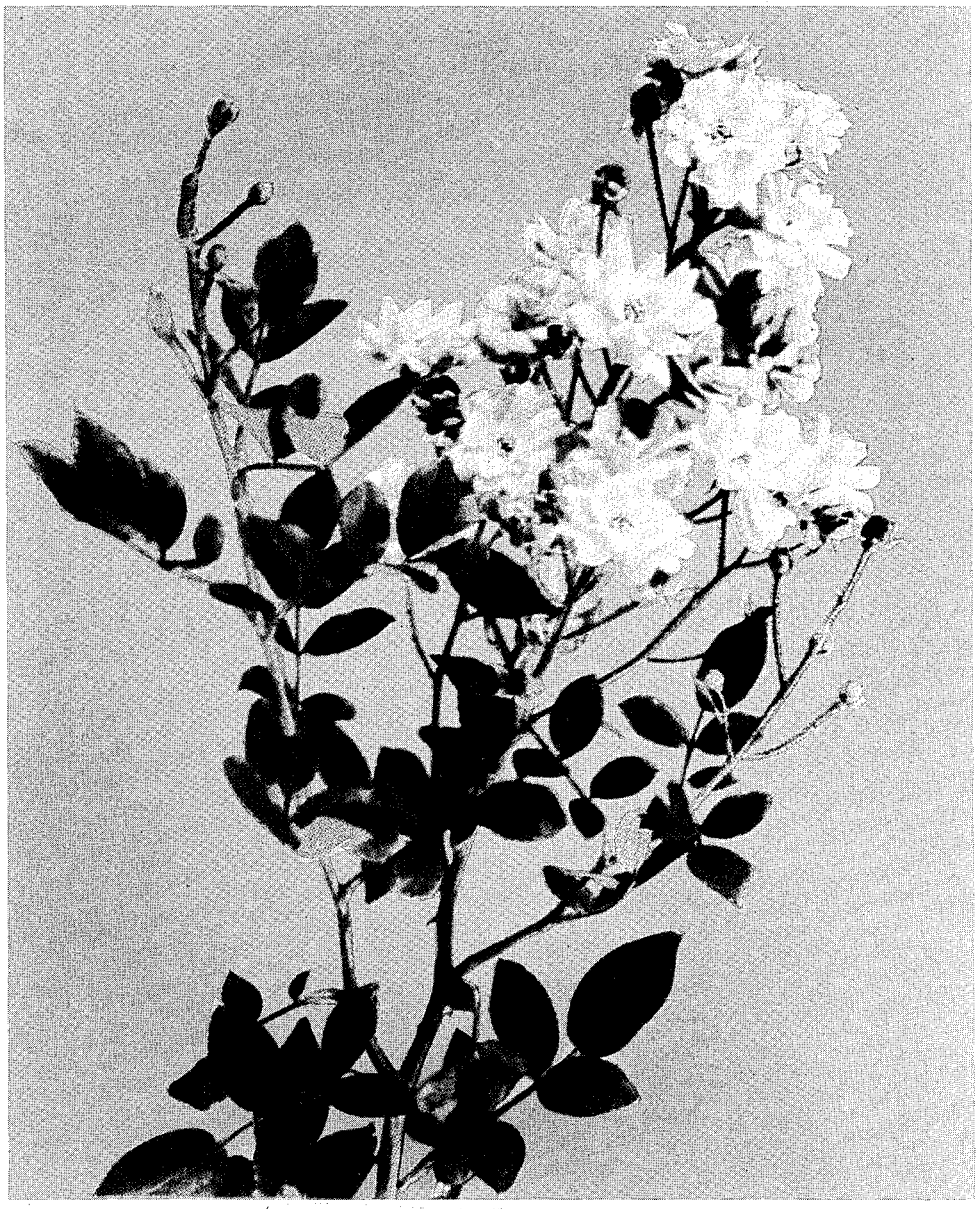
Inventor
G. de Ruiter
By Robb & Robb
Attorneys Patented July 22, 1947

UNITED STATES PATENT OFFICE

746

ROSE PLANT

Gerrit de Ruiter, Hazerswoude, Netherlands, assignor to Jackson & Perkins Company, Newark, N. Y., a corporation of New York Application December 8, 1942, Serial No. 468,295

1 Claim. (Cl. 47—61)

The present invention relates to a new and distinct variety of rose plant, belonging to the polyantha group or class and originating as a sport of an unnamed "Orleans" variety sport. More specifically, this new variety was developed by the discovery of one flower of the type herein disclosed in a cluster of an "Orleans" flower and by the use of this one, the new variety color was developed in successive years. In other respects of the flowers and general growth, the characteristics are similar to the original "Orleans" rose.

The development of this new variety I deem important because of its special excellent forcing qualities, and more particularly because of the new and distinct color of the blossoms for this type of polyantha, the color referred to being a close approach to Thulite Pink, as hereinafter more specifically stated.

Asexual reproduction shows the dominant characteristics herein set forth to be established.

The following is a detailed description of this new rose, the color terminology employed hereing being in accord with Ridgway's Color Standard:

Parentage:

*Parent variety.*—Sport of unnamed "Orleans" sport.

Classification:

*Botanic and commercial.*—Polyantha.

*Flower*

(Observations made in the greenhouse of Jackson & Perkins Company, Newark, New York.)

Blooming habit: Recurrent—continuous.

Bud:

*Size.*—Small.

*Form.*—Short with flat top. Is not affected by wet or hot weather.

*Color.*—When sepals first divide—between Pomegranate Purple, Plate 12, and Rose Red, Plate 12. When petals begin to unfurl—between Spinel Red, Plate 26, and Spinel Pink, Plate 26. When half blown—inside of petals, between Rose Color, Plate 12, and Deep Rose Pink, Plate 12; reverse of petals, between Spinel Pink, Plate 26, and Thulite Pink, Plate 26.

*Sepals.*—Branched. Curl back when petals unfurl. Color—upper side, Rainette Green, Plate 31; under side, Kildare Green, Plate 31.

*Calyx.*—Shape—funnel. Size—small. Aspect—smooth. Odor when rubbed—none. Color—Light Cress Green, Plate 31.

*Peduncle.*—Length—short. Aspect—prickly. Color—Light Cress Green, Plate 31. Strength—erect; slender.

*Opening.*—Bud opens well. Is not affected by adverse conditions.

Bloom:

*Size.*—Small. Average size when fully expanded, 1½".

*Borne.*—In clusters, pyramidal.

*Stems.*—Short; normal.

*Form.*—When first open—flat. Permanence—retains its form to the end.

*Petalage.*—Double (full but open center). Number of petals under normal conditions, 20.

*Color.*—Center of flower—between Spinel Pink, Plate 26, and Thulite Pink, Plate 26, with lower portion near stamens Cameo Pink, Plate 26. Outer petals—between Thulite Pink, Plate 26, and Spinel Pink, Plate 26. Base of petals (aiglet)—Marguerite Yellow, Plate 30. Inside of petals—between Thulite Pink, Plate 26, and Spinel Pink, Plate 26. Reverse of petals—Deep Rose Pink, Plate 12. General tonality from a distance—Spinel Pink, Plate 26.

*Discoloration.*—General tonality at end of first day—between Spinel Pink, Plate 26, and Thulite Pink, Plate 26. Second day—Between Spinel Pink, Plate 26, and Thulite Pink, Plate 26. Third day—Thulite Pink, Plate 26.

Petals:

*Texture.*—Thin. Is not affected by wet or hot weather.

*Appearance.*—Inside—velvety. Outside—shiny.

*Form.*—Notched

*Arrangement.*—Irregular. Petaloids in center—few; small.

*Persistence.*—Drop off cleanly.

*Fragrance.*—None.

*Lasting quality.*—On the plant and as cut flower—long.

Genital organs:

*Stamens, anthers.*—Small; many. Color—Apricot Yellow, Plate 4. Arrangement—regular around styles.

*Stamens, filaments (threads).*—Short. Color—Martius Yellow, Plate 4.

*Pollen.*—Buff Yellow, Plate 4.

*Styles.*—Bunched; even; medium length; thin.

*Stigmas.*—Martius Yellow, Plate 4.

*Ovaries.*—All enclosed in calyx.

*Plant*

Form: Bush.
Growth: Vigorous; branching.
Foliage: 5–7 leaflets.
*Size.*—Medium.
*Quantity.*—Normal.
*Color.*—New foliage—upper side, Elm Green, Plate 17; under side, Jade Green, Plate 31. Old foliage—upper side, Cress Green, Plate 31; under side, Light Cress Green, Plate 31.
*Shape.*—Oval pointed.
*Texture.*—Upper side—leathery. Under side—smooth. Ribs and veins—ordinary.
*Edge.*—Serrated (saw toothed).
*Serration.*—Single; small.
*Rachis.*—Light Cress Green, Plate 31. Under side—smooth.
*Stipules.*—Short; branched slightly.
*Disease resistance.*—Resistant.
Wood:
*New wood.*—Color—Absinthe Green, Plate 31. Bark—rough.

*Old wood.*—Color—Light Cress Green, Plate 31. Bark—smooth.
Thorns (thorns are divided into thorns, prickles, and short needles):
*Thorns.*—Quantity—on main stalks from base and on laterals from stalk, few. Form—flat base; short; hooked downward. Color when young—Mignonette Green, Plate 31. Position—in pairs.
*Prickles.*—On main stalks and on laterals—none.
*Short needles.*—On main stalks and on laterals—none.

I claim:

A new and distinct variety of rose plant of the polyantha class characterized as to novelty by its excellent forcing qualities and the new and distinct pink coloring of the flower clusters for a rose of the polyantha class, substantially as shown and described.

GERRIT DE RUITER.